(12) United States Patent
Kan et al.

(10) Patent No.: US 11,369,442 B2
(45) Date of Patent: Jun. 28, 2022

(54) SURGICAL SYSTEM

(71) Applicants: MEDICAROID CORPORATION, Kobe (JP); KABUSHIKI KAISHA TOP, Tokyo (JP); KAWASAKI JUKOGYO KABUSHIKI KAISHA, Kobe (JP)

(72) Inventors: Kazutoshi Kan, Kobe (JP); Takuya Miyazaki, Tokyo (JP); Yoshihiko Himura, Tokyo (JP)

(73) Assignees: MEDICAROID CORPORATION, Kobe (JP); KABUSHIKI KAISHA TOP, Tokyo (JP); KAWASAKI JUKOGYO KABUSHIKI KAISHA, Kobe (JP)

( * ) Notice: Subject to any disclaimer, the term of this patent is extended or adjusted under 35 U.S.C. 154(b) by 438 days.

(21) Appl. No.: 16/364,107

(22) Filed: Mar. 25, 2019

(65) Prior Publication Data

US 2019/0216556 A1 Jul. 18, 2019

Related U.S. Application Data

(63) Continuation of application No. PCT/JP2016/080565, filed on Oct. 14, 2016.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/37* (2016.02); *A61B 34/71* (2016.02); *A61B 90/50* (2016.02);
(Continued)

(58) Field of Classification Search
CPC ..... A61B 1/0055; A61B 1/0008; A61B 34/70; A61B 90/50; A61B 1/00071;
(Continued)

(56) References Cited

U.S. PATENT DOCUMENTS

| 4,683,882 A * | 8/1987 | Laird ................ A61M 16/0488 |
| | | 128/207.17 |
| 10,271,874 B2 * | 4/2019 | Wada ................ A61B 17/3494 |

(Continued)

FOREIGN PATENT DOCUMENTS

| JP | 2004-041580 | * | 2/2004 | ....... A61B 2034/301 |
| JP | 2008-237812 A | | 10/2008 | |

(Continued)

OTHER PUBLICATIONS

A English translation of the International Search Report of PCT/JP2016/080565 dated Nov. 22, 2016.

(Continued)

*Primary Examiner* — Diane D Yabut
*Assistant Examiner* — Christina C Lauer
(74) *Attorney, Agent, or Firm* — Metrolex IP Law Group, PLLC

(57) ABSTRACT

A surgical system includes: a plurality of surgical instruments each of which includes a flexible shaft provided with a surgical tool on a leading end-side portion thereof, a supporting platform that supports the plurality of surgical instruments; a medical instrument that includes a plurality of flexible inner tubes into which the flexible shafts of the surgical instruments can be inserted, and an outer tube into which the plurality of flexible inner tubes can be inserted and that is to be inserted into a body cavity; and a gripping mechanism that includes a gripping portion that grips the outer tube, and a supporting portion that includes at least one joint portion and that fixes and supports the gripping portion, (Continued)

the at least one joint portion making the medical instrument adjustable regarding the position and orientation thereof.

13 Claims, 11 Drawing Sheets

(51) Int. Cl.
  *A61B 34/37* (2016.01)
  *A61B 17/00* (2006.01)
  *A61B 90/50* (2016.01)

(52) U.S. Cl.
  CPC ............... *A61B 2017/00477* (2013.01); *A61B 2034/301* (2016.02); *A61B 2034/302* (2016.02); *A61B 2034/306* (2016.02)

(58) Field of Classification Search
  CPC ............ A61B 1/00147; A61B 17/3421; A61B 2034/301; A61B 1/0051; A61B 34/30; A61B 34/71; A61B 34/37
  See application file for complete search history.

(56) References Cited

U.S. PATENT DOCUMENTS

| | | |
|---|---|---|
| 2006/0161136 A1 | 7/2006 | Anderson et al. |
| 2008/0243176 A1 | 10/2008 | Weitzner et al. |
| 2009/0171374 A1* | 7/2009 | Omori .................... A61B 34/30 606/130 |
| 2009/0192520 A1 | 7/2009 | Finlay |
| 2010/0004509 A1* | 1/2010 | Naito .................. A61B 1/00133 600/141 |
| 2011/0004157 A1 | 1/2011 | Dewaele et al. |
| 2011/0071347 A1 | 3/2011 | Rogers et al. |
| 2014/0277741 A1 | 9/2014 | Kwon et al. |
| 2015/0250546 A1 | 9/2015 | Larkin et al. |
| 2016/0143633 A1 | 5/2016 | Robert et al. |
| 2016/0331402 A1 | 11/2016 | Wada et al. |

FOREIGN PATENT DOCUMENTS

| | | |
|---|---|---|
| JP | 2009-160011 A | 7/2009 |
| JP | 2009-183698 A | 8/2009 |
| JP | 2013-138965 A | 7/2013 |
| JP | 2013-223751 A | 10/2013 |
| JP | 2014-180751 A | 9/2014 |
| JP | 2015-077466 A | 4/2015 |
| JP | 2016-528946 A | 9/2016 |
| WO | 2015/107994 A1 | 7/2015 |

OTHER PUBLICATIONS

A English translation of the International Search Report dated Dec. 6, 2016 in a related International application No. PCT/JP2016/080567, which was submitted with Information Disclosure Statement on Mar. 25, 2019 in co-pending U.S. Appl. No. 16/364,143.

* cited by examiner

SURGICAL SYSTEM

CROSS-REFERENCE TO RELATED APPLICATION

This application is based upon and claims the benefit of priority from International Application No. PCT/JP2016/080565, filed on Oct. 14, 2016, the disclosure of which is incorporated herein in its entirety by reference.

BACKGROUND OF THE INVENTION

Technical Field

The present invention relates to a surgical system that includes a gripping mechanism for gripping a medical instrument.

Description of Related Art

Conventionally, surgery on a part inside a body cavity is performed by inserting an endoscope and a treatment tool such as a pair of forceps or a scalpel into the body cavity. As a medical instrument for such surgery, there is a known endoscope treatment device that includes an endoscope, the aforementioned treatment tool which is used under observation with the endoscope, a plurality of inner tubes into each of which the endoscope and the treatment tool can be inserted so as to be able to move back and forth, and an outer tube into which the inner tubes can be inserted (for example, see WO 2015/107994 (Patent Document 1)).

However, when surgery is to be performed using a medical instrument that includes an outer tube into which inner tubes can be inserted, as described above, the medical instrument is attached to the body by, for example, inserting the outer tube into a trocar that is held on the body surface, by inserting the medical instrument into a mouthpiece as described in Patent Document 1, or by an assistant or the like holding the medical instrument by his/her hand. Therefore, an operator needs to get used to attaching or holding the medical instrument, and there is the possibility of shake, displacement, or the like.

SUMMARY OF THE INVENTION

The present invention has been made to solve the above-described problem, and aims to provide a surgical system that makes it possible to perform more desirable treatment using a medical instrument that includes an outer tube into which inner tubes can be inserted.

A surgical system according to one aspect of the present invention includes: a plurality of surgical instruments each of which includes a flexible shaft provided with a surgical tool on a leading end-side portion thereof, a supporting platform that supports the plurality of surgical instruments; a medical instrument that includes a plurality of flexible inner tubes into which the flexible shafts of the surgical instruments can be inserted, and an outer tube into which the plurality of flexible inner tubes can be inserted and that is to be inserted into a body cavity; and a gripping mechanism that includes a gripping portion that grips the outer tube, and a supporting portion that includes at least one joint portion and that fixes and supports the gripping portion, the at least one joint portion making the medical instrument adjustable regarding the position and orientation thereof.

According to the present invention, it is possible to perform more desirable treatment using a medical instrument that includes an outer tube into which inner tubes can be inserted.

The foregoing and other objects, features, aspects and advantages of the present invention will become more apparent from the following detailed description of the present invention when taken in conjunction with the accompanying drawings.

DESCRIPTION OF EMBODIMENTS

Figure 1:
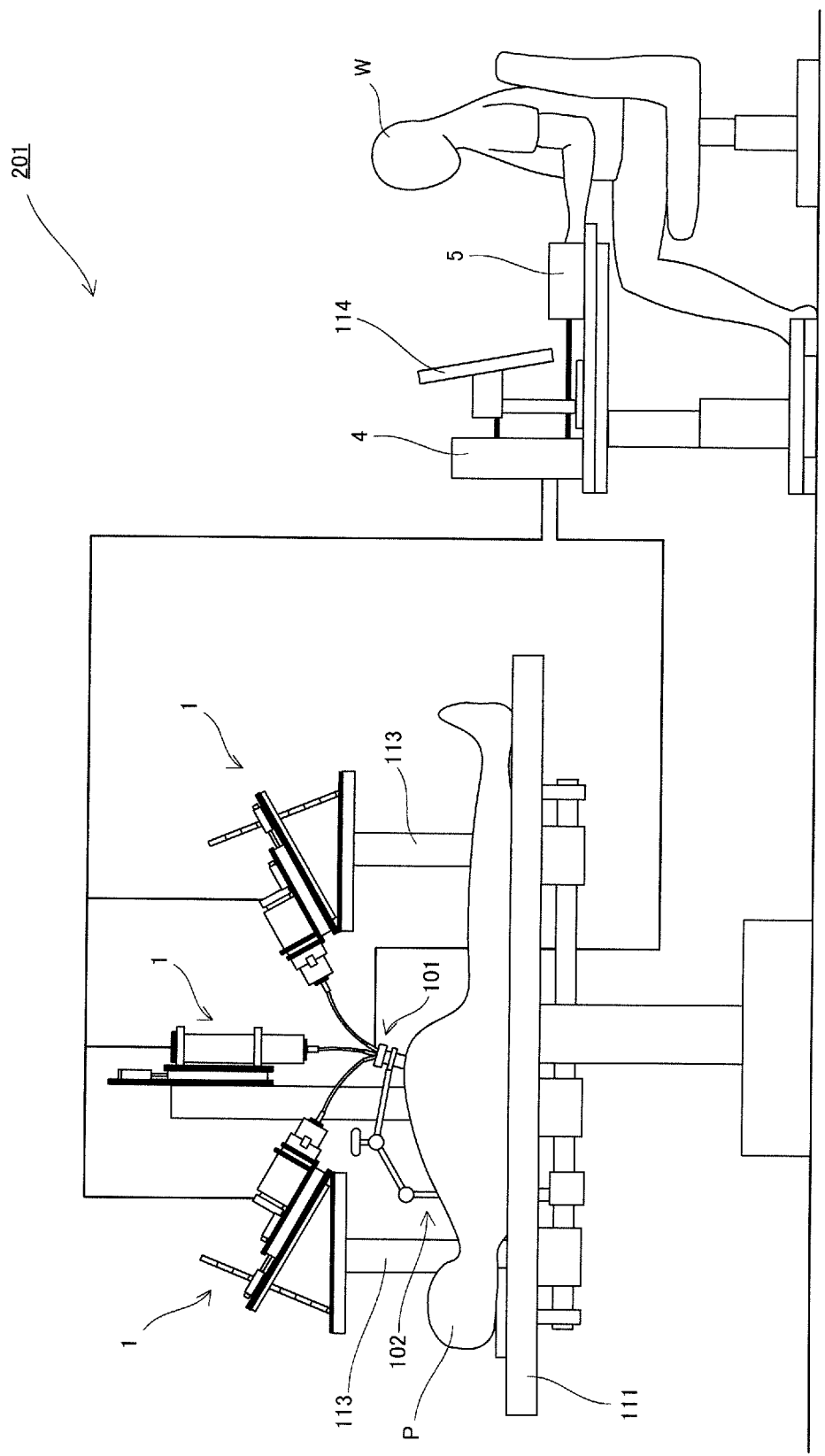
FIG. 1 shows a configuration of a surgical system according to an embodiment of the present invention.

First, details of an embodiment of the present invention are listed and described below.

(1) A gripping mechanism according to an embodiment of the present invention is a gripping mechanism that grips a medical instrument that includes: an inner tube into which a surgical instrument can be inserted and that is flexible; and an outer tube into which one or more inner tubes can be inserted and that is to be inserted into a body cavity. The gripping mechanism includes a gripping portion that grips the outer tube, and a supporting portion that fixes and supports the gripping portion. The supporting portion includes at least one joint portion that makes the medical instrument adjustable regarding the position and orientation thereof.

With such a configuration, it is possible to freely adjust the position and orientation of the medical instrument gripped by the gripping portion. Therefore, it is possible to perform more desirable treatment using the medical instrument that includes the outer tube into which the inner tube can be inserted.

(2) Preferably, an opening portion into which the outer tube can be inserted is formed in the grip portion, and the grip portion includes an adjustment mechanism that can change the diameter of the opening portion.

With such a configuration, even if outer tubes with different outer diameters are used depending on where the medical instrument is to be inserted, it is possible to grip any of such outer tubes by changing the diameter of the opening portion depending on which outer tube is to be used.

(3) More preferably, the adjustment mechanism is an adjustment member that is attachable to, and detachable from, the opening portion, and the diameter of the opening portion can be changed by attaching or detaching the adjustment member to or from the opening portion.

With such a configuration, it is possible to provide the opening portion with various diameters.

(4) More preferably, the adjustment mechanism is a claw portion that is formed so as to be able to protrude toward a central point of the opening portion, and the amount of protrusion of the claw portion is changeable.

With such a configuration, it is easier to change the diameter of the opening portion without using a large number of members.

(5) Preferably, the medical instrument is an instrument that is to be used in laparoscopic surgery.

In a case of laparoscopic surgery, for example, a medical instrument is inserted into the body cavity of the patient via an incision formed in the body surface. Therefore, it is difficult to fix the position and orientation of the medical instrument compared to when a medical instrument is inserted via a natural orifice such as the mouth. Thus, a gripping mechanism that grips a medical instrument as described above is particularly effective for gripping a medical instrument that is to be used in laparoscopic surgery.

(6) Preferably, a guide portion that guides the inner tube so as to be inserted into the outer tube is provided in the outer tube.

With such a configuration, it is easier to insert the inner tube into the outer tube. Also, in a state where the inner tube is inserted into the outer tube, the positional relationship between the inner tube and the outer tube can be kept the same even when the position or the orientation of the medical instrument is changed.

(7) Preferably, the gripping portion is ring-shaped.

With such a configuration it is possible to lower the likelihood that the gripping portion will be brought into contact with another instrument or an operator, even if the position or the orientation of the gripping portion is changed.

(8) Preferably, the supporting portion includes a coupling in which a plurality of arm portions are coupled to each other via the joint portion.

With such a configuration, it is possible to more precisely adjust the position and orientation of the medical instrument.

(9) More preferably, the supporting portion further includes a connecting portion that connects the coupling and the gripping portion to each other.

With such a configuration, it is possible to realize a gripping mechanism that grips the medical instrument at any position and in any orientation without employing a complex configuration.

(10) More preferably, the connecting portion is rod-shaped, and extends from an outer circumferential surface of the gripping portion.

With such a configuration, it is easier to connect the connecting portion to a structure.

(11) Preferably, the gripping portion includes a plurality of constituent members that can be coupled to each other, an opening portion into which the outer tube can be inserted is formed by coupling the plurality of constituent members to each other, and the gripping mechanism further includes a fixing member for fixing the plurality of constituent members in a state of being coupled to each other.

With such a configuration, it is easier to attach or detach the outer tube by decoupling the plurality of constituent members from each other and increasing the diameter of the opening portion, for example. Also, as described above, it is possible to use the fixing member to fix the plurality of constituent members in a state of being coupled to each other. Therefore, it is possible to more reliably grip the outer tube.

(12) Preferably, the supporting portion further includes a coupling and a connecting portion that connects the coupling and the gripping portion to each other, and the fixing member and the connecting portion oppose each other with the opening portion interposed therebetween.

With such a configuration, the position of the fixing member does not significantly change even if the gripping portion is rotated about the connecting portion to change the orientation of the medical instrument, for example. Therefore, it is possible to lower the likelihood that the fixing member will be brought into contact with another instrument, or an operator or the like, regardless of the orientation of the medical instrument.

A medical instrument according to an embodiment of the present invention includes an inner tube into which a surgical instrument can be inserted and that is bendable in response to the action of an operational element; an outer tube into which one or more inner tubes can be inserted and that is to be inserted into a body cavity; and an inner tube drive mechanism that electrically controls the operational element.

With such a configuration, it is possible to bend the inner tube by operating the inner tube drive mechanism, without manually bending the inner tube. Therefore, it is possible to more accurately and easily bend the inner tube. Also, in a case where the inner tube is to be straightened so that the surgical instrument can be inserted into the inner tube, the inner tube can be accurately straightened. Therefore, it is easier to insert the surgical instrument into the inner tube. Thus, it is possible to perform more desirable treatment using the medical instrument that includes the outer tube into which the inner tube can be inserted.

Preferably, the inner tube drive mechanism receives a drive instruction signal, and electrically controls the operational element based on the received drive instruction signal.

With such a configuration, it is possible to remotely bend the inner tube. Therefore, for example, a surgeon who is in a place away from a patient can perform an operation to bend the inner tube, in addition to operating the surgical instrument. Thus, it is possible to improve operability.

More preferably, the drive instruction signal is provided by a remote operation device that is provided in a remote location.

With such a configuration, for example, a surgeon can bend the inner tube by operating the remote operation device.

More preferably, the drive instruction signal indicates the inclination of the inner tube.

With such a configuration, it is possible to bend the inner tube to any inclination by specifying the inclination in the drive instruction signal, for example.

Preferably, the inner tube drive mechanism includes a motor, and the motor electrically controls the operational element.

With such a configuration, it is easier to bend the inner tube by utilizing the rotation of the motor. Also, it is possible to change the inclination of the inner tube stepwise by adjusting the rotation of the motor.

Preferably, the inner tube drive mechanism includes a gear to which the operational element is connected.

With such a simple configuration in which the gear is rotated and thus the operational element is caused to perform an action, it is possible to accurately and easily bend the inner tube.

More preferably, the operational element is a wire, and the inner tube drive mechanism receives a drive instruction signal, and draws back or sends out the wire by driving the gear using the motor based on the received drive instruction signal.

With such a simpler configuration, it is possible to accurately and easily bend the inner tube.

Preferably, the surgical instrument includes a multi-joint portion, and, in a state where the surgical instrument is inserted into the inner tube, the multi-joint portion can be bent in a direction opposite the direction in which the inner tube is bent.

With such a configuration, it is possible to widen the range of motion of the surgical instrument. Therefore, it is possible to freely change the position and orientation of a surgical tool provided at the leading end of the surgical instrument, relative to the surgical site.

A surgical system according to an embodiment of the present invention includes: a gripping mechanism that includes a grip portion that grips the outer tube of the medical instrument, and a supporting portion that fixes and supports the gripping portion at a constant position; and the medical instrument.

A medical instrument that includes an inner tube drive mechanism is heavy, and it is difficult to grip the medical instrument by using a conventional cannula or by hand. Therefore, as described above, it is particularly effective that the gripping mechanism that grips the outer tube of the medical instrument is employed.

The following describes an embodiment of the present invention with reference to the drawings. Note that the same portions and equivalent portions in the drawings are assigned the same reference numerals and the descriptions thereof are not repeated. At least some portions of the embodiment below may be combined in any manner.

Overall Configuration

FIG. 1 shows a configuration of a surgical system 201 according to an embodiment of the present invention.

As shown in FIG. 1, a surgical system 201 is a remote surgical system with which a surgeon W remotely operates surgical instruments 1 and a medical instrument 101, and performs minimally invasive surgery using the surgical instruments 1 inserted into the body of a patient P on a treatment table 111.

Each surgical instrument 1 is supported on a supporting platform 113 attached to the treatment table 111, for example. Each surgical instrument 1 includes flexible shafts that are elongated, and multi-joint surgical tools are coupled to leading end-side portions of the flexible shafts.

The surgical instruments 1, the medical instrument 101, and an operation unit (remote operation device) 5 are electrically connected to a controller 4. Upon being operated by the surgeon W, the operation unit 5 provides the surgical instruments 1 and the medical instrument 101 with action instructions via the controller 4. Thus, it is possible to remotely operate the surgical instruments 1 and the medical instrument 101.

Figure 2:
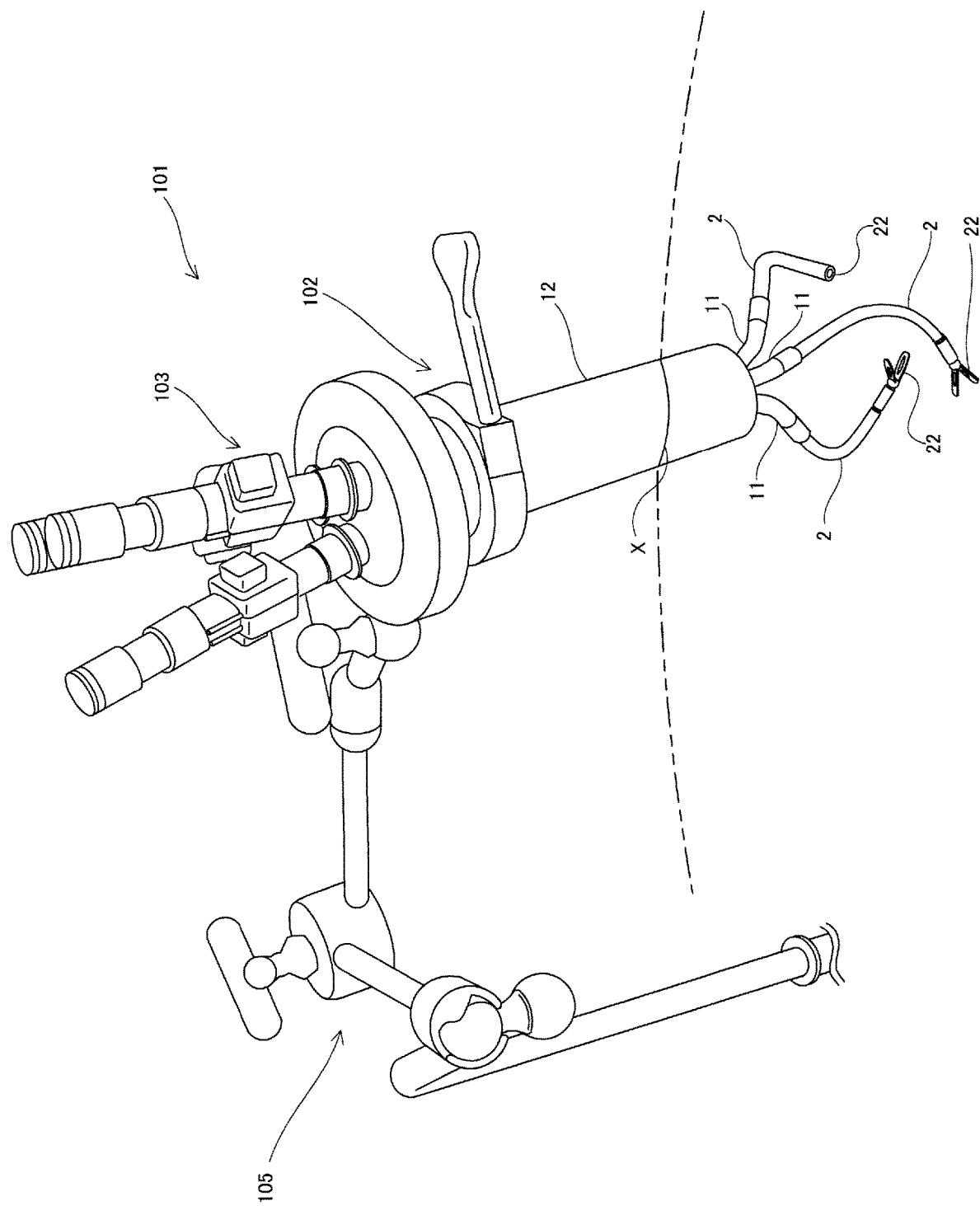
FIG. 2 is an enlarged perspective view of configurations of a medical instrument and a gripping mechanism shown in FIG. 1.

FIG. 2 is an enlarged perspective view of configurations of the medical instrument 101 and a gripping mechanism 102 shown in FIG. 1.

As shown in FIG. 2, the medical instrument 101 is an instrument that is used in endoscope surgery or the like, and includes one or more inner tubes 11 into each of which a surgical instrument 1 is inserted, an outer tube 12, and an inner tube drive mechanism 103. A flexible shaft 2 and a surgical tool 22 provided on a leading end-side portion of a surgical instrument 1 are inserted into each inner tube 11 of the medical instrument 101.

For example, when laparoscopic surgery is to be performed, the medical instrument 101 is inserted into the body cavity of the patient via an incision X formed in the body surface. Note that the medical instrument 101 may be inserted into the body of the patient via a natural orifice such as the mouth instead of being inserted via the incision X. In other words, the medical instrument 101 may be used not only in laparoscopic surgery, but also in natural orifice transluminal endoscopic surgery or the like.

Each inner tube 11 is tubular and flexible. Also, each inner tube 11 can be bent in response to the action of operational elements included in the inner tube drive mechanism 103. The outer tube 12 has a tubular shape with an inner diameter greater than the outer diameter of the inner tubes 11, and is flexible. One or more inner tubes 11 are inserted into the outer tube 12. A plurality of types of outer tubes 12 with different outer diameters are prepared, for example.

Specifically, when laparoscopic surgery is to be performed, an outer tube 12 with an outer diameter of 20 mm to 40 mm is typically used. When natural orifice transluminal endoscopic surgery is to be performed, an outer tube 12 with an outer diameter of approximately 20 mm is typically used.

The inner tube drive mechanism 103 electrically controls operational elements for bending the inner tubes 11.

A gripping mechanism 102 grips the outer circumferential surface of a base end-side portion of the outer tube 12 of the medical instrument 101, i.e. a portion that is not inserted into the body surface, to fix the position and orientation of the medical instrument 101. The gripping mechanism 102 includes a coupling 105 that is provided near the treatment table 111, for example.

Medical Instrument

Figure 3:
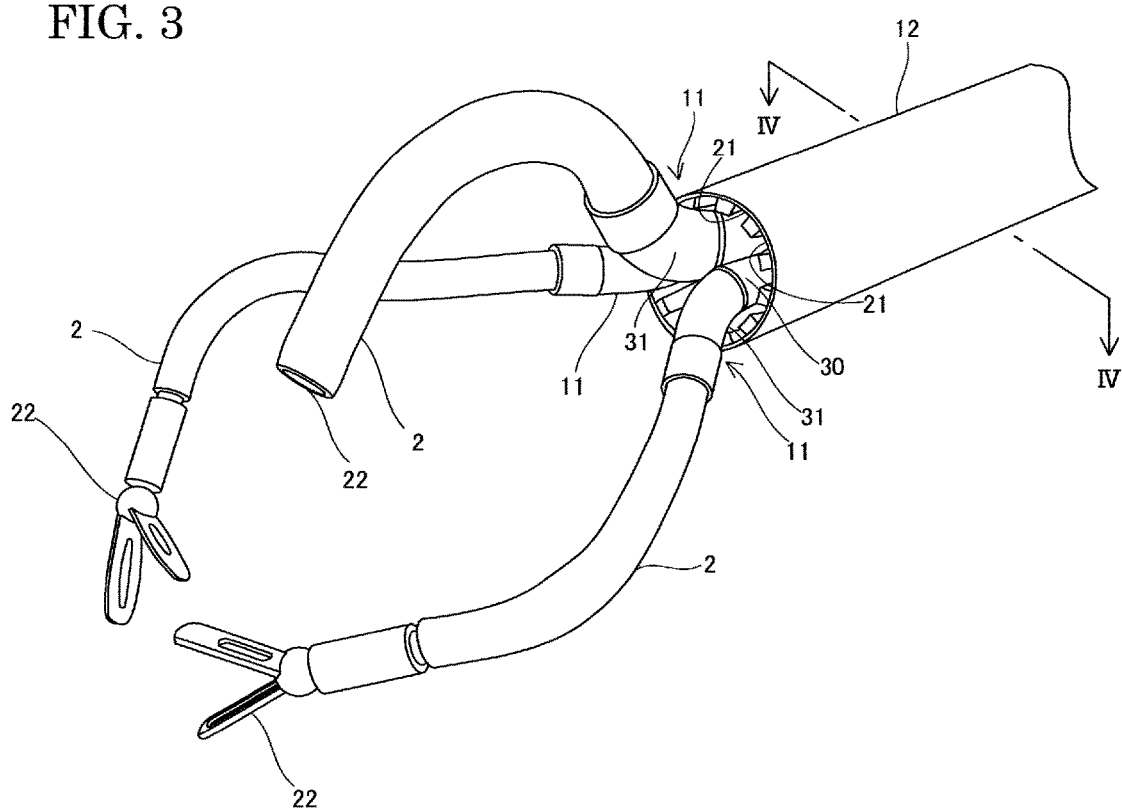
FIG. 3 is a perspective view showing a state in which inner tubes are inserted into an outer tube.
Figure 4:
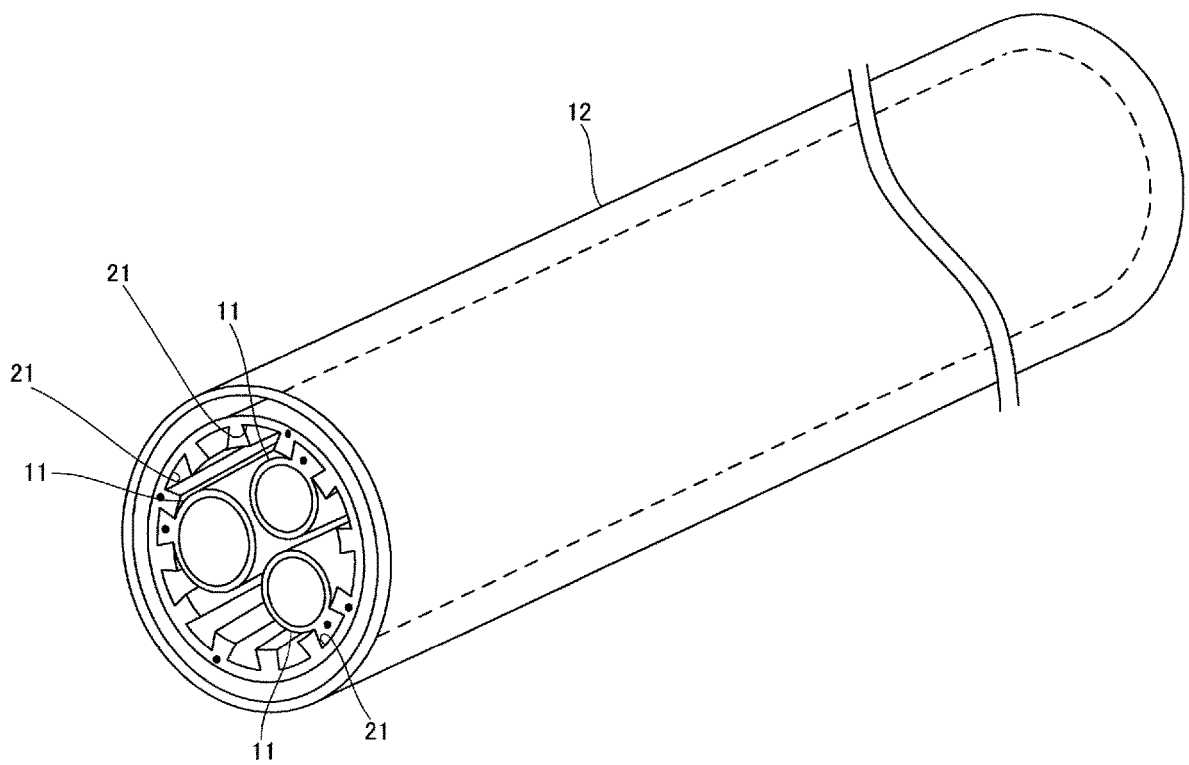
FIG. 4 is a cross-sectional perspective view showing a cross section taken along a IV-IV line shown in FIG. 3.

FIG. 3 is a perspective view showing a state in which inner tubes 11 are inserted into an outer tube 12. FIG. 4 is a cross-sectional perspective view showing a cross section taken along a IV-IV line shown in FIG. 3.

As shown in FIGS. 3 and 4, the outer tube 12 includes one or more guide portions 21 that each guide an inner tube 11. Each guide portion 21 is, for example, a mortise that extends along the inner wall of the outer tube 12 in the axial direction of the outer tube 12. As shown in FIG. 4, each guide portion 21 has a substantially trapezoidal cross section that gradually widens in a direction from the inner circumferential surface to the outer circumferential surface of the outer tube 12.

Figure 5:
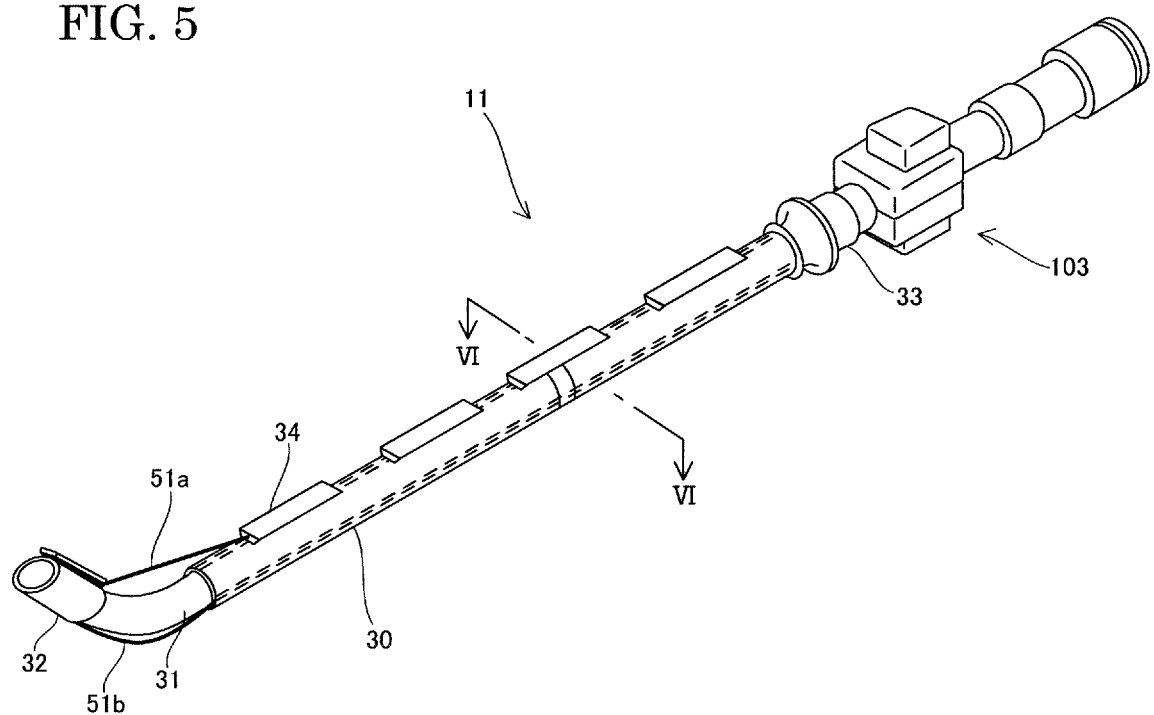
FIG. 5 is a perspective view showing a configuration of an inner tube according to an embodiment of the present invention.

FIG. 5 is a perspective view showing a configuration of an inner tube 11 according to an embodiment of the present invention.

As shown in FIG. 5, each inner tube 11 includes a shaft portion 30 that is somewhat hard and is flexible, a bendable portion 31, a leading end portion 32, and a base end portion 33. Each inner tube 11 also includes engagement portions 34 that extend at intervals along the outer circumferential surface of the shaft portion 30 in the axial direction.

In a state where an inner tube 11 is inserted into the outer tube 12, at least a portion of the bendable portion 31 and the leading end portion 32 are exposed from the outer tube 12. Also, in a state where an inner tube 11 is inserted into the outer tube 12, the bendable portion 31 is bendable in response to the action of the inner tube drive mechanism 103.

Figure 6:
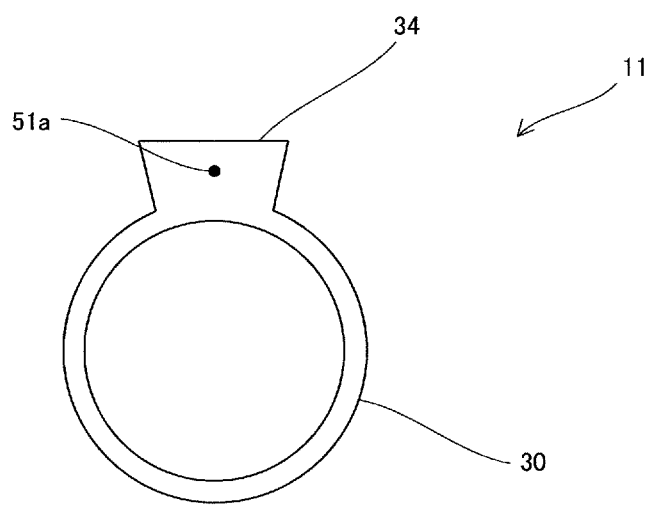
FIG. 6 is a cross-sectional view showing a cross section taken along a VI-VI line shown in FIG. 5.

FIG. 6 is a cross-sectional view showing a cross section taken along a VI-VI line shown in FIG. 5.

As shown in FIG. 6, each engagement portion 34 has a substantially trapezoidal cross section that gradually widens in a direction from the inner circumferential surface to the outer circumferential surface of the inner tube 11.

When an inner tube 11 is inserted into the outer tube 12, the engagement portions 34 engage with a guide portion 21 of the outer tube 12 so as to be slidable. Thus, in a state where inner tubes 11 are inserted into the outer tube 12, the positional relationship between the inner tubes 11 and the outer tube 12 can be kept the same even when the position or the orientation of the medical instrument 101 is changed.

A wire member 51a, which is an operational element, is inserted through the engagement portions 34. As shown in FIG. 5, one end-side portion of the wire member 51a is fixed to the leading end portion 32 of the inner tube 11. It is possible to bend the bendable portion 31 by causing the other end-side portion of the wire member 51a to perform a draw-back action or a send-out action.

As shown in FIG. 5, the engagement portions 34 provided at intervals are suitable for a case where inner tubes 11 are inserted into, and removed from, a bent outer tube 12. However, the engagement portions 34 may be continuously provided in the axial direction of the shaft portion 30.

In a case where there is no need to accurately keep the positional relationship between the outer tube 12 and the inner tubes 11 the same when adjusting the position or angle of the medical instrument 101, the outer tube 12 may not be provided with the above-described guide portions 21, and the inner tubes 11 may not be provided with the above-described engagement portions 34.

With reference to FIG. 3 again, although wire members 51a and 51b are provided as operational elements for operating the inner tubes 11, a plurality of rods, a plurality of flat plates, or a combination of rods and flat plates, which are coupled to each other so as to be bendable, may be used instead of the wire members 51a and 51b, for example.

Also, a combination of a wire member 51a and a plurality of rods or a plurality of flat plates may be used as operational elements. For example, portions that are inserted through the engagement portions 34 may be the wire member 51a, and exposed portions that connect an engagement portion 34 and the leading end portion 32 may be a plurality of rods that are coupled to each other so as to be bendable.

Surgical Instrument

Figure 7:
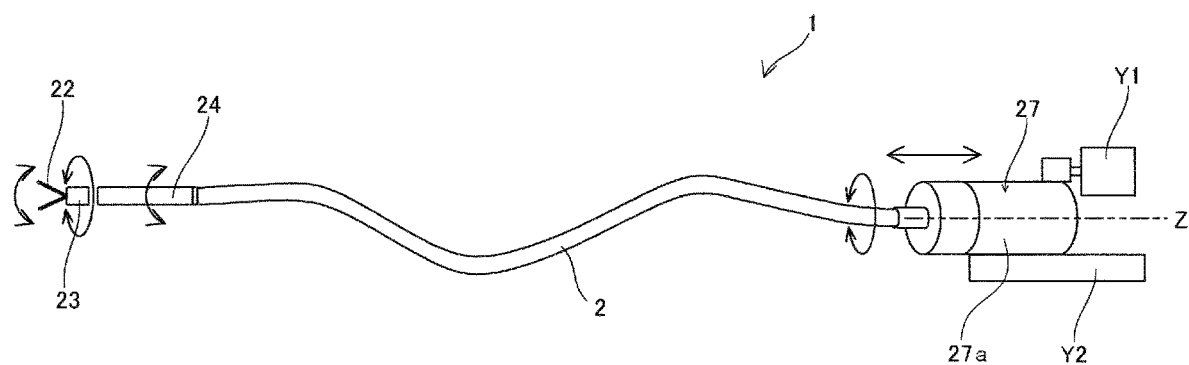
FIG. 7 is a schematic diagram showing an example of a configuration of a surgical instrument.

FIG. 7 is a schematic diagram showing an example of a configuration of a surgical instrument 1.

As shown in FIG. 7, each surgical instrument 1 includes a surgical tool 22 at the leading end, such as a pair of forceps, a wrist joint portion 23, a multi-joint portion 24, a flexible shaft 2, and a surgical instrument drive mechanism 27.

A plurality of motors such as servomotors are built into a housing 27a of the surgical instrument drive mechanism 27. The plurality of motors are respectively coupled to the surgical tool 22 and the multi-joint portion 24 via wires, and to the wrist joint portion 23 via a torque transmission tube. Thus, the surgical instrument drive mechanism 27 can drive the surgical tool 22, the multi-joint portion 24, and the wrist joint portion 23 independent of each other.

The surgical instrument drive mechanism 27 is also coupled to eternal motors Y1 and Y2 provided outside the housing 27a of the surgical instrument drive mechanism 27 via a gear mechanism or the like. The surgical instrument drive mechanism 27 rotates about the axis of the flexible shaft 2, i.e. about the Z axis shown in FIG. 7, upon the external motor Y1 driving, and the surgical instrument drive mechanism 27 slides in the axial direction of the flexible shaft 2 upon the external motor Y2 driving.

Thus, the action of the leading end portion of each surgical instrument 1 according to the present invention has five degrees of freedom as indicated by arrows in FIG. 7. Note that the action of the leading end portion of each surgical instrument 1 may have six degrees of freedom with the multi-joint portion 24 being divided into a first multi-joint portion and a second multi-joint portion, or four degrees of freedom with the rotation of the surgical instrument drive mechanism 27 being omitted. Thus, the surgical instruments 1 are not limited to five degrees of freedom.

Figure 8:
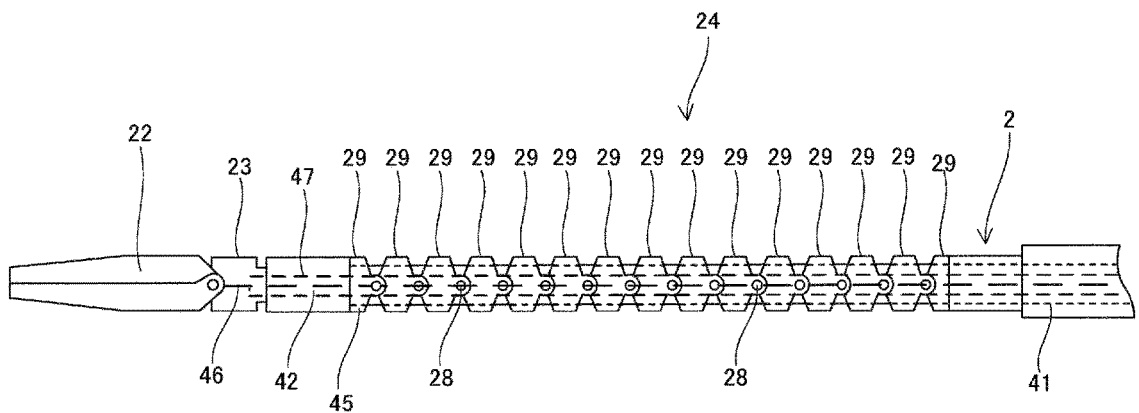
FIG. 8 is a detailed diagram showing a configuration of a leading end-side portion of a surgical instrument.

FIG. 8 is a detailed diagram showing a configuration of a leading end-side portion of a surgical instrument 1.

As shown in FIG. 8, the multi-joint portion 24 includes a plurality of segment members 29 that are coupled to each other via pins 28 and are lined up in the axial direction. Each segment member 29 has the shape of a cylinder that extends in the axial direction of the multi-joint portion 24. Each segment member 29 is tapered such that the thickness of the segment member 29 in the axial direction gradually decreases in two directions away from the axis of the segment member 29.

Multi-joint operation cables 41 are respectively inserted through two side portions of each segment member 29, which are located away from the axis of the segment member 29, so as to be parallel with the axis of the segment member 29. One end of each multi-joint operation cable 41 is fixed to a leading end-side fixed end 45 of the continuous segment members 29, and the other end of each multi-joint operation cable 41 is connected to a motor in the surgical instrument drive mechanism 27. One of the multi-joint operation cables 41 respectively inserted through the two side portions of each segment member 29 is drawn back and the other is sent out, and thus the surgical tool 22 can be orientated in a desired direction.

Also, a torque transmission tube 47 is inserted through a portion near the axis, of each segment member 29. One end of the torque transmission tube 47 is fixed to the wrist joint portion 23, and the other end is fixed to a motor in the surgical instrument drive mechanism 27. The torque transmission tube 47 can transmit torque applied to the other end of the tube to the one end, and thus the wrist joint portion 23 can be rotated about the axes of the segment members 29.

Furthermore, a surgical tool operation cable 46 is inserted through a portion near the axis, of each segment member 29. A first end of the surgical tool operation cable 46 is coupled to a surgical tool operator (not shown), and a second end of the surgical tool operation cable 46 is connected to a motor in the surgical instrument drive mechanism 27. For example, in a case where the surgical tool 22 is a pair of gripping forceps, it is possible to realize an opening and closing action of the gripping forceps by performing an operation to draw back or send out the surgical tool operation cable 46.

Note that the surgical tool 22 is a pair of forceps, a scalpel, a hook, an endoscope, or the like, and the action is not limited to an opening and closing action, and a rotating action may be performed.

Inner Tube Drive Mechanism

Next, a detailed configuration of the inner tube drive mechanism 103 will be described.

Figure 9:
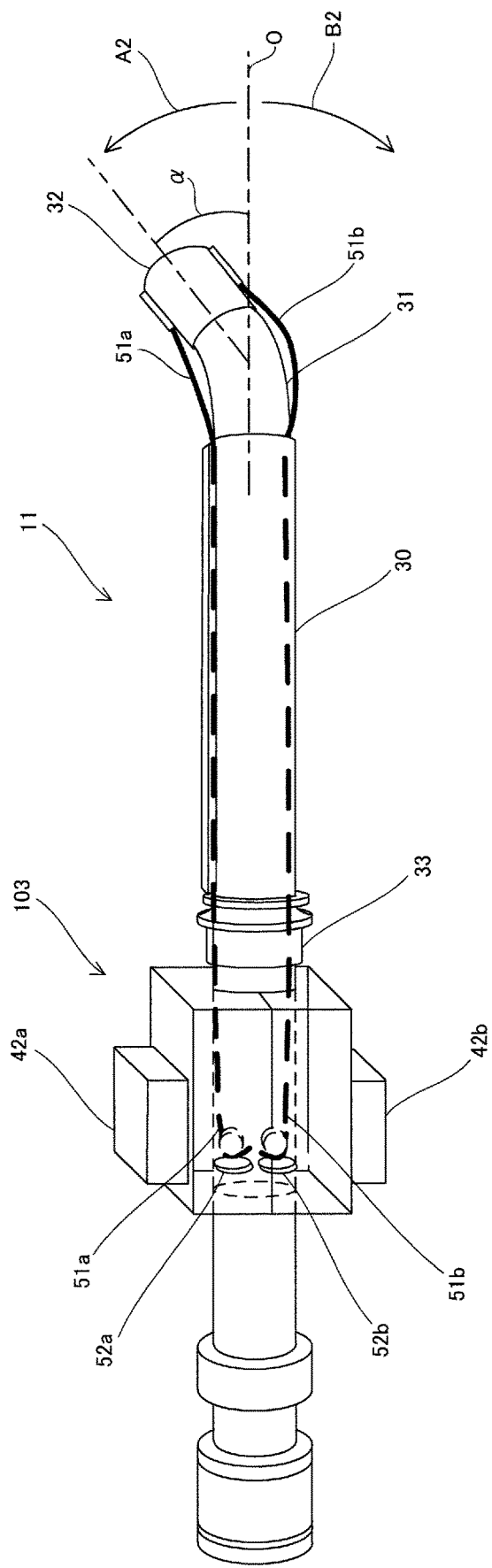
FIG. 9 is a perspective view showing a configuration of an inner tube drive mechanism according to an embodiment of the present invention.

FIG. 9 is a perspective view showing a configuration of an inner tube drive mechanism 103 according to an embodiment of the present invention.

As shown in FIG. 9, the inner tube drive mechanism 103 includes inner tube drive motors 42a and 42b, the wire members 51a and 51b that are operational elements provided so as to extend in the axial direction of the inner tube 11, and gear portions 52a and 52b that are provided in the base end portion 33 of the inner tube 11.

First ends of the wire members 51a and 51b are fixed to the leading end portion 32 of the inner tube 11. Also, the wire members 51a and 51b extend outside the bendable portion 31, pass through the shaft portion 30, and second ends thereof are fixed to the gear portions 52a and 52b.

The inner tube drive motors 42a and 42b rotate the gear portions 52a and 52b in response to action instructions provided via the controller 4 upon the operation unit 5 being operated, for example.

As described above, the degree of operational freedom can be increased by one degree by providing the inner tube drive mechanism 103 that includes the inner tube drive motors 42a and 42b. In the case of the surgical instrument 1 illustrated in FIGS. 7 and 8, the degree of operational freedom can be increased from five degrees to six degrees.

Also, the degree of bend of the inner tube 11 can be freely changed and fixed stepwise by providing the inner tube drive mechanism 103 that includes the inner tube drive motors 42a and 42b.

Method for Operating Surgical System

Figure 10:
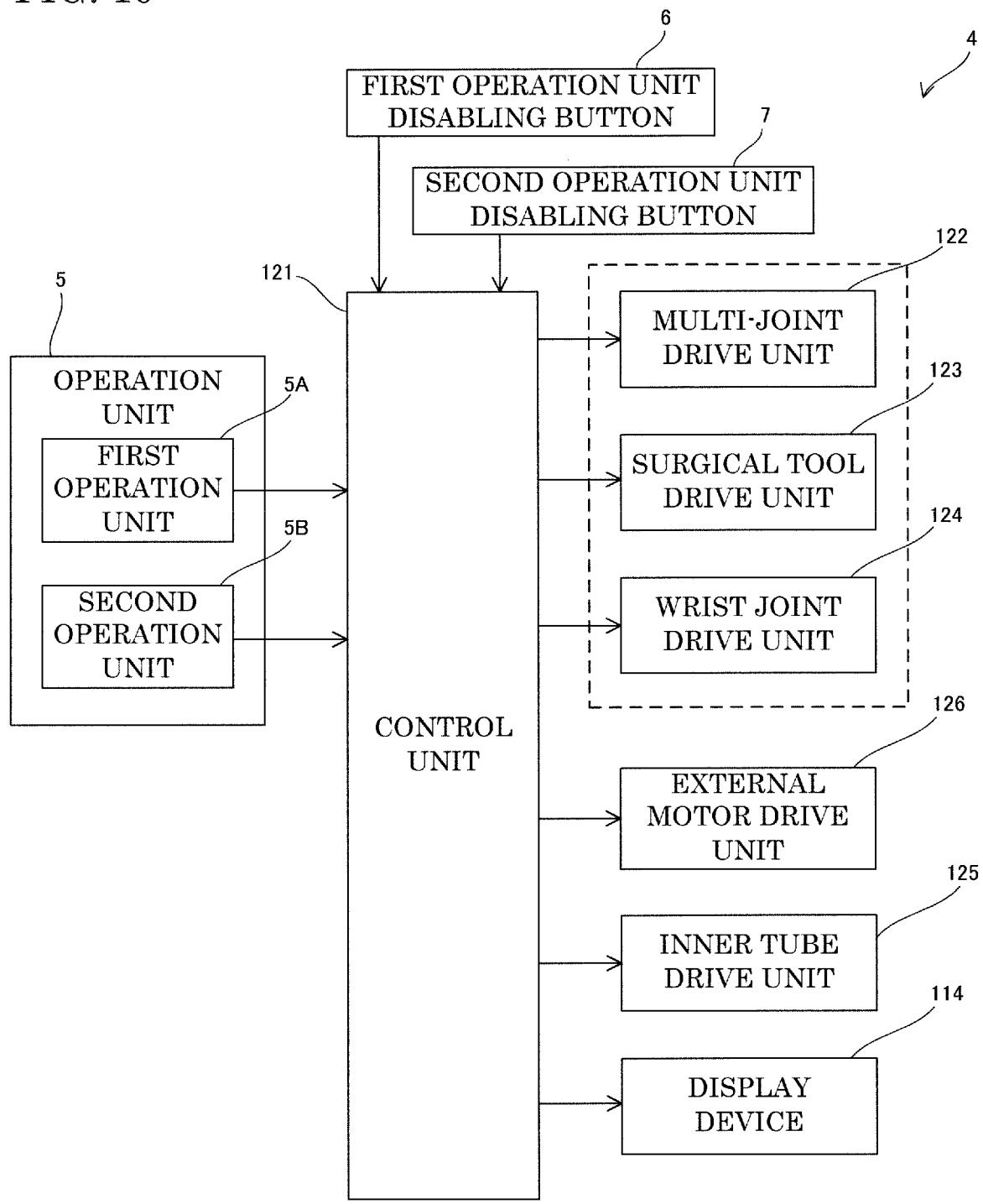
FIG. 10 is a block diagram showing an example of a configuration of a controller.

FIG. 10 is a block diagram showing an example of a configuration of a controller 4.

As shown in FIG. 10, the controller 4 includes a computing unit such as a CPU. The controller 4 may be constituted by a single controller that performs centralized control, or a plurality of controllers that cooperate with each other to perform distributed control.

The operation unit 5 is operated by the surgeon W, and is for inputting action instructions that are to be executed by the medical instrument 101 and the surgical instruments 1 to perform actions. The operation unit 5 is configured to be able to perform wired or wireless communication with the controller 4. The operation unit 5 converts action instructions input by the surgeon W and to be executed by the medical instrument 101 and the surgical instruments 1 to data, and transmits the data to the controller 4. Then, the controller 4 remotely controls the actions of the medical instrument 101 and the surgical instruments 1 through wired or wireless communication, based on the action instruction data received from the operation unit 5.

Specifically, the controller 4 includes a control unit 121, a multi-joint drive unit 122, a surgical tool drive unit 123, a wrist joint drive unit 124, an inner tube drive unit 125, and an external motor drive unit 126. Upon receiving action instruction data from the operation unit 5, the control unit 121 in the controller 4 outputs the received action instruction data to a drive unit corresponding thereto among the multi-joint drive unit 122, the surgical tool drive unit 123, the wrist joint drive unit 124, the inner tube drive unit 125, and the external motor drive unit 126.

The multi-joint drive unit 122, upon receiving action instruction data from the control unit 121, provides the surgical instrument driving mechanism 27 with an action instruction based on the action instruction data, to drive the multi-joint portion 24. The surgical tool drive unit 123, upon receiving action instruction data from the control unit 121, provides the surgical instrument driving mechanism 27 with an action instruction based on the action instruction data, to drive the surgical tool 22. The wrist joint drive unit 124, upon receiving action instruction data from the control unit 121, provides the surgical instrument driving mechanism 27 with an action instruction based on the action instruction data, to drive the wrist joint portion 23.

The external motor drive unit 126, upon receiving action instruction data from the control unit 121, provides external motors Y1 and Y2 with action instructions based on the action instruction data, to drive the external motors Y1 and Y2.

The inner tube drive unit 125, upon receiving action instruction data from the control unit 121, provides the inner tube drive motors 42a and 42b in the inner tube drive mechanism 103 with action instructions based on the action instruction data, to bend the inner tube 11.

The control unit 121 also displays the details of action instruction data received from the operation unit 5 on a display device 114, for example.

The operation unit 5 includes, for example, a first operation unit 5A for providing the surgical instrument driving mechanism 27 with an action instruction, and a second operation unit 5B for providing the inner tube drive motors 42a and 42b in the inner tube drive mechanism 103 with action instructions.

Figure 11:
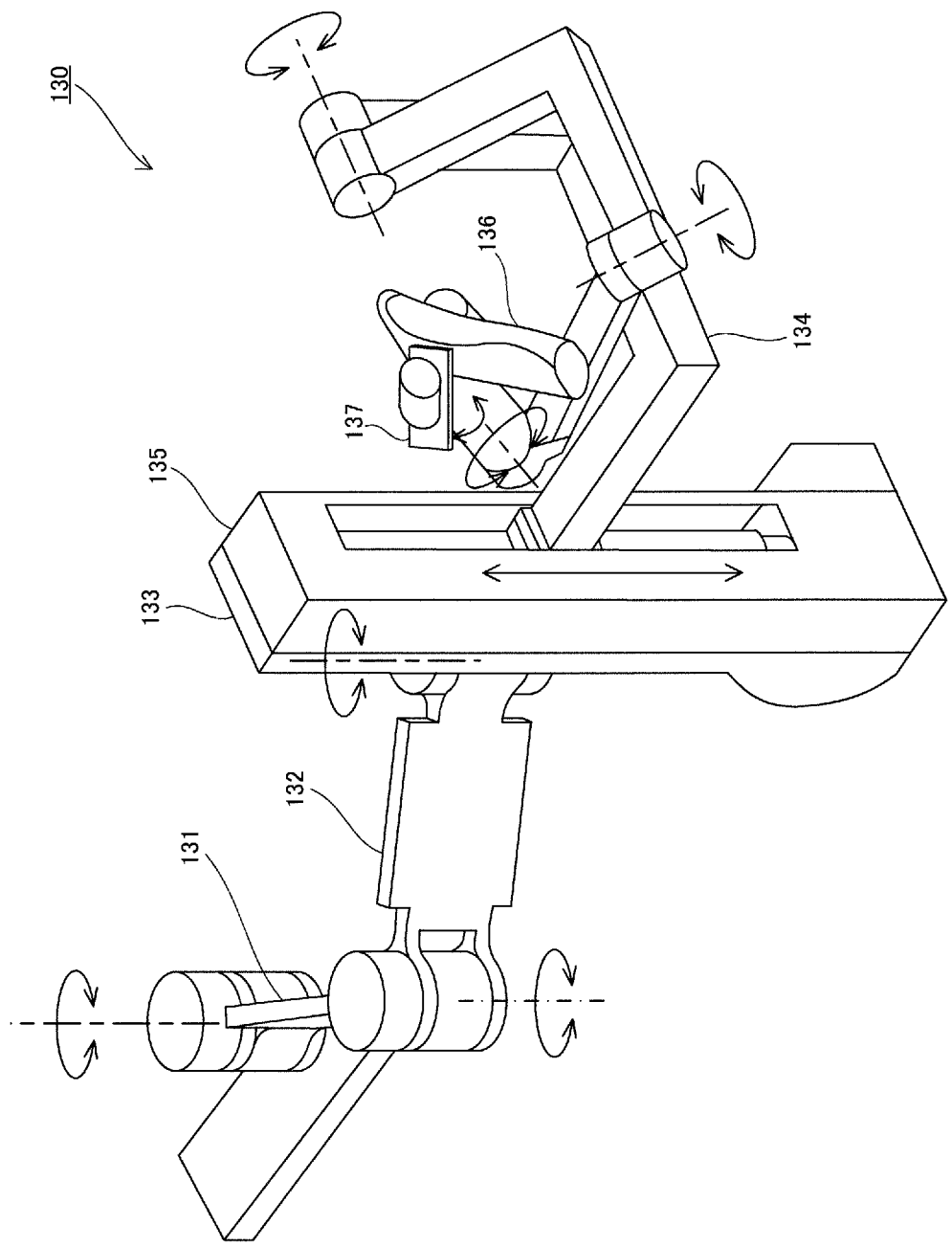
FIG. 11 is a diagram showing an example of a configuration of a hand control that serves as a first operation unit.

FIG. 11 is a diagram showing an example of a configuration of a hand control 130 that serves as a first operation unit 5A.

As shown in FIG. 11, a hand control 130 includes a plurality of link members 131, 132, 133, and 134, a lifting/lowering guide 135, and a hand grip 136, which are coupled to each other via rotary or prismatic joints. The hand control 130 also includes a hand grip 137 that is coupled to the hand grip 136 so as to be able to open and close. With such a configuration, the hand control 130 can perform operational input with a maximum of eight degrees of freedom.

Note that it is possible to reduce the degree of freedom by operating the link members 131 and 132 in conjunction with each other, or reduce the degree of freedom by one or two degrees by omitting at least one of the link members 131 and 132, for example.

Figure 12:
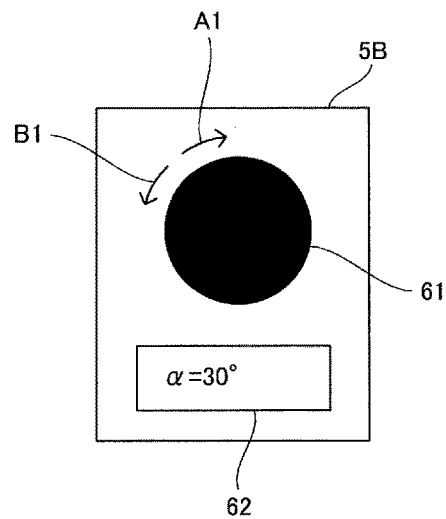
FIG. 12 is a diagram showing an example of a configuration of a second operation unit.
Figure 13:
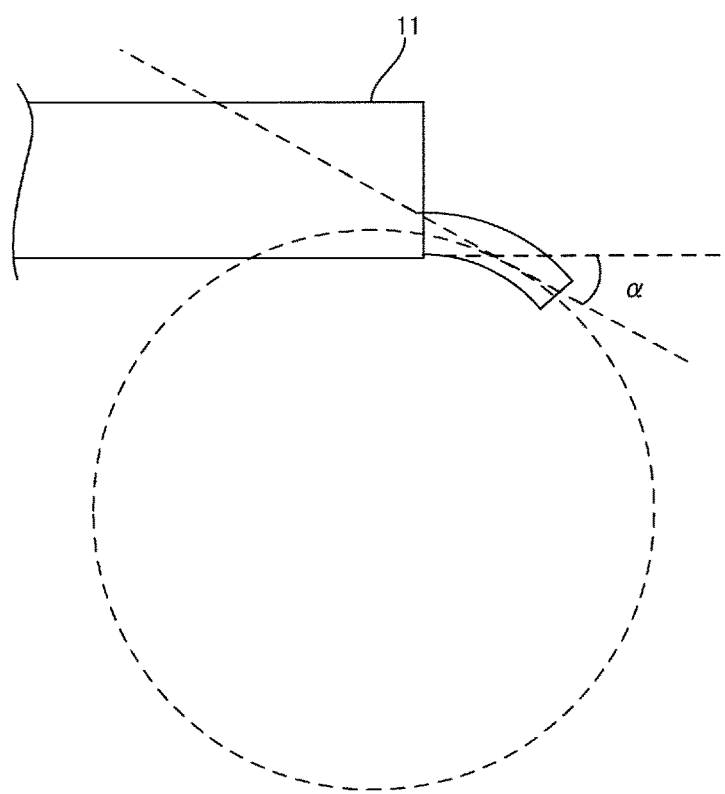
FIG. 13 is a diagram showing the angle of inclination of an inner tube.

FIG. 12 is a diagram showing an example of a configuration of a second operation unit 5B. The second operation unit 5B is provided adjacent to the first operation unit 5A, for example. FIG. 13 is a diagram showing the angle of inclination of an inner tube 11.

As shown in FIG. 12, the second operation unit 5B includes a rotary knob 61 and a display unit 62, for example. The inner tube drive motors 42a and 42b operate in conjunction with the rotation of the rotary knob 61 of the second operation unit 5B.

Specifically, upon the surgeon or the like rotating the rotary knob 61, the value of an angle α corresponding to the rotation angle of the rotary knob 61 is displayed on the display unit 62.

Note that the value of the angle α may be the same as, or different from, the value of the rotation angle of the rotary knob 61. Also, the display unit 62 may display the level of inclination corresponding to the rotation angle of the rotary knob 61, such as "large", "medium", or "small", instead of the angle α, which is a specific value.

A drive instruction signal indicating the angle α corresponding to the rotation angle of the rotary knob 61 or the level of inclination corresponding to the rotation angle of the rotary knob 61 is transmitted to each of the inner tube drive motors 42a and 42b in the inner tube drive mechanism 103 through wired or wireless communication via the controller 4.

The inner tube drive motor 42b draws back the wire member 51a by rotating the gear portion 52a by an angle corresponding to 30° indicated by a drive instruction signal, for example. As a result, the bendable portion 31 inclines by the angle α, i.e. 30°, relative to a central axis O of the shaft portion 30, in the direction indicated by an arrow A2 shown in FIG. 9.

Note that the direction in which the inner tube 11 is bent is an in-plane direction with respect to a plane that includes the wire member 51a, the wire member 51b, and the central axis O of the shaft portion 30, and the angle α is, as shown in FIG. 13, the angle of a tangent to the curvature of a leading end portion of the inner tube 11.

For example, upon the surgeon or the like rotating the rotary knob 61 by 30° in the direction indicated by an arrow A1 shown in FIG. 12, "30°" is displayed on the display unit 62 as the angle α, and the controller 4 transmits a drive instruction signal indicating "30°" to each of the inner tube drive motors 42a and 42b.

Also, for example, upon the surgeon or the like rotating the rotary knob 61 by 30° in the direction indicated by an arrow B1 shown in FIG. 12, "−30°" is displayed on the display unit 62 as the angle α, and the controller 4 transmits a drive instruction signal indicating "−30°" to each of the inner tube drive motors 42a and 42b.

The inner tube drive motor 42b draws back the wire member 51b by rotating the gear portion 52b by an angle corresponding to 30° indicated by a drive instruction signal, for example. As a result, the bendable portion 31 inclines by the angle α, i.e. 30°, relative to the central axis O of the shaft portion 30, in the direction indicated by an arrow B2 shown in FIG. 9.

Note that, at the same time as controlling the angle of bend of the inner tube 11 as described above, the controller 4 may perform control to bend the multi-joint portion 24 of the surgical instrument 1 in a direction opposite the direction in which the inner tube 11 is bent. For example, the controller 4 performs control to bend the multi-joint portion 24 in the opposite direction by the same angle as the angle of bend of the inner tube 11. Thus, it is possible to widen the range of motion of the surgical instruments 1. Therefore, it is possible to freely change the position and orientation, i.e. the approach angle, of the surgical tools 22 relative to the surgical site such as an organ of the patient P.

With reference to FIG. 10 again, in order to avoid unintentionally operating the first operation unit 5A and causing the surgical instrument 1 to perform an erroneous action, it is preferable that a first operation unit disabling button 6 is provided to disable the first operation unit 5A from being operated when the second operation unit 5B is operated. Also, for the same reason, it is preferable that a second operation unit disabling button 7 is provided to disable the second operation unit 5B from being operated when the first operation unit 5A is operated.

Also, the first operation unit 5A and the second operation unit 5B may be configured to be operated in conjunction with each other. For example, when one of the first operation unit 5A and the second operation unit 5B is disabled from being operated, the other may also be disabled from being operated, by the controller 4 controlling output of action instruction data.

Although the inner tube drive mechanism 103 shown in FIG. 9 includes two wire members and two inter tube drive motors, the inner tube drive mechanism 103 may include one wire member and one inner tube drive motor. If two wire members and two inner tube drive motors are included, when the inner tube 11 is to be restored from a bent state to a straight state, it is possible to accurately and swiftly restore the inner tube 11 to a straight state without leaving the effect of the bent state by drawing back and sending out the wire members at the same time, using the individual inner tube drive motors. Thus, the surgical instrument 1 can be easily replaced, and the efficiency of surgery can be improved.

Also, the second operation unit 5B may be omitted and the first operation unit 5A may be configured to serve as the second operation unit 5B. For example, it is possible to operate the surgical instrument 1 and the inner tube 11 with a single hand control 130 as shown in FIG. 11 by performing computation so that the surgical instrument 1 shown in FIGS. 7 and 8, which has five degrees of operational freedom, can be operated with six degrees of freedom resulting from the addition of the bending freedom of the inner tube 11.

The second operation unit 5B may be provided with, for example, a "bend button" for bending the inner tube 11 and a "straightening button" for straightening the inner tube 11, instead of the rotary knob 61.

Specifically, upon the surgeon W or the like performing an operation to select the "bending button" of the second operation unit 5B, a drive instruction signal that indicates a predetermined angle β is transmitted to the controller 4. Then, the controller 4 drives the inner tube drive motors 42a and 42b based on the received drive instruction signal, and performs control such that the inclination of the bendable portion 31 equals the angle β, for example.

Also, upon the surgeon W or the like performing an operation to select the "straitening button" of the second operation unit 5B, a drive instruction signal that indicates "0°" is transmitted to the controller 4. Then, the controller 4 drives the inner tube drive motors 42a and 42b based on the received drive instruction signal, and performs control such that the inclination of the bendable portion 31 equals "0°", for example.

As described above, according to the embodiment of the present invention, it is possible to remotely operate the inner tube drive motors 42a and 42b in the inner tube drive mechanism 103, using the operation unit 5.

Note that it is also possible to provide the inner tube drive motors 42a and 42b with drive switches and actuate the inner tube drive motors 42a and 42b by directly turning the drive switches ON/OFF, instead of remotely operating the inner tube drive motors 42a and 42b.

Gripping Mechanism

Next, a detailed configuration of the gripping mechanism 102 will be described.

Figure 14:
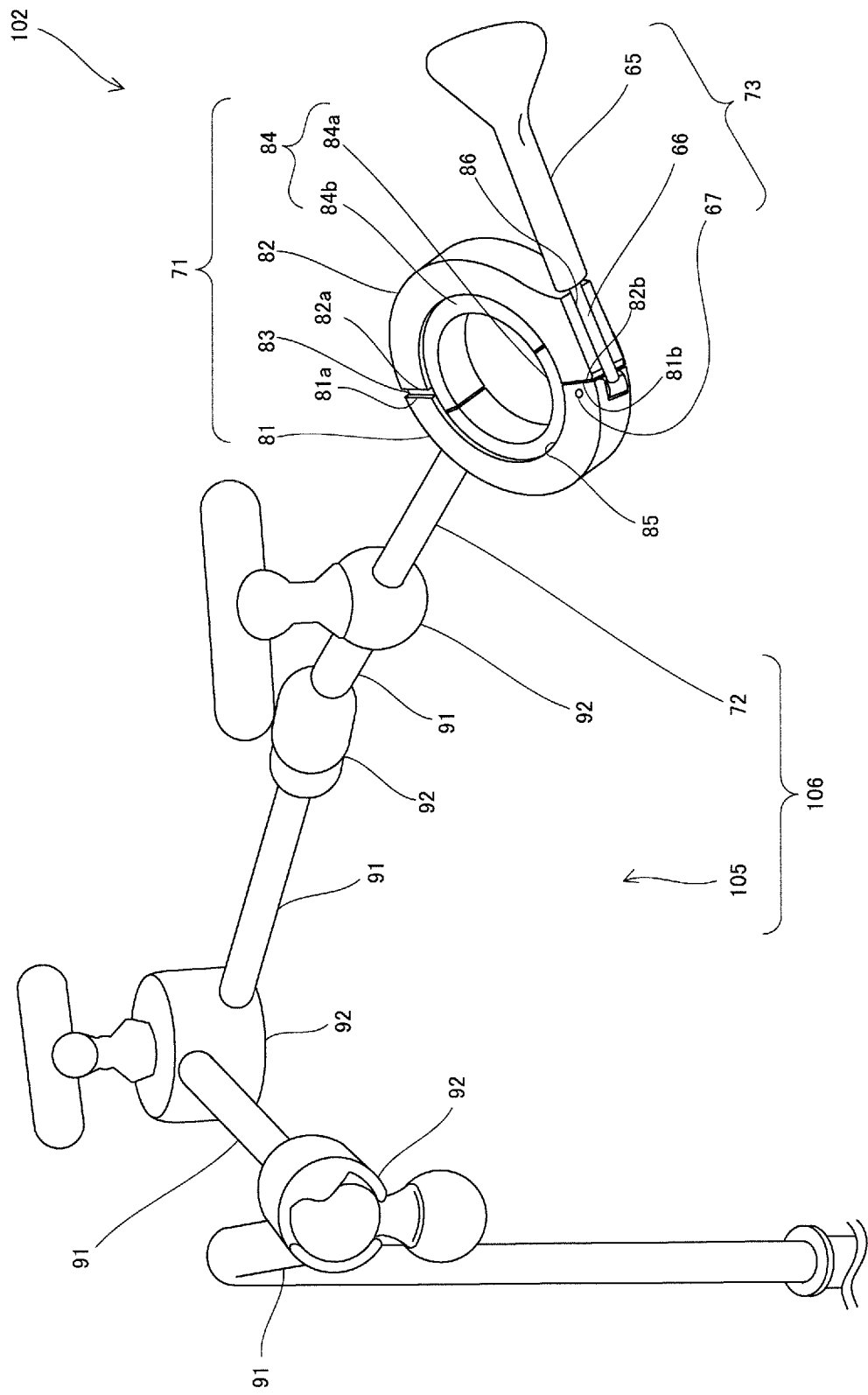
FIG. 14 is a perspective view showing the gripping mechanism according to an embodiment of the present invention.
Figure 15:
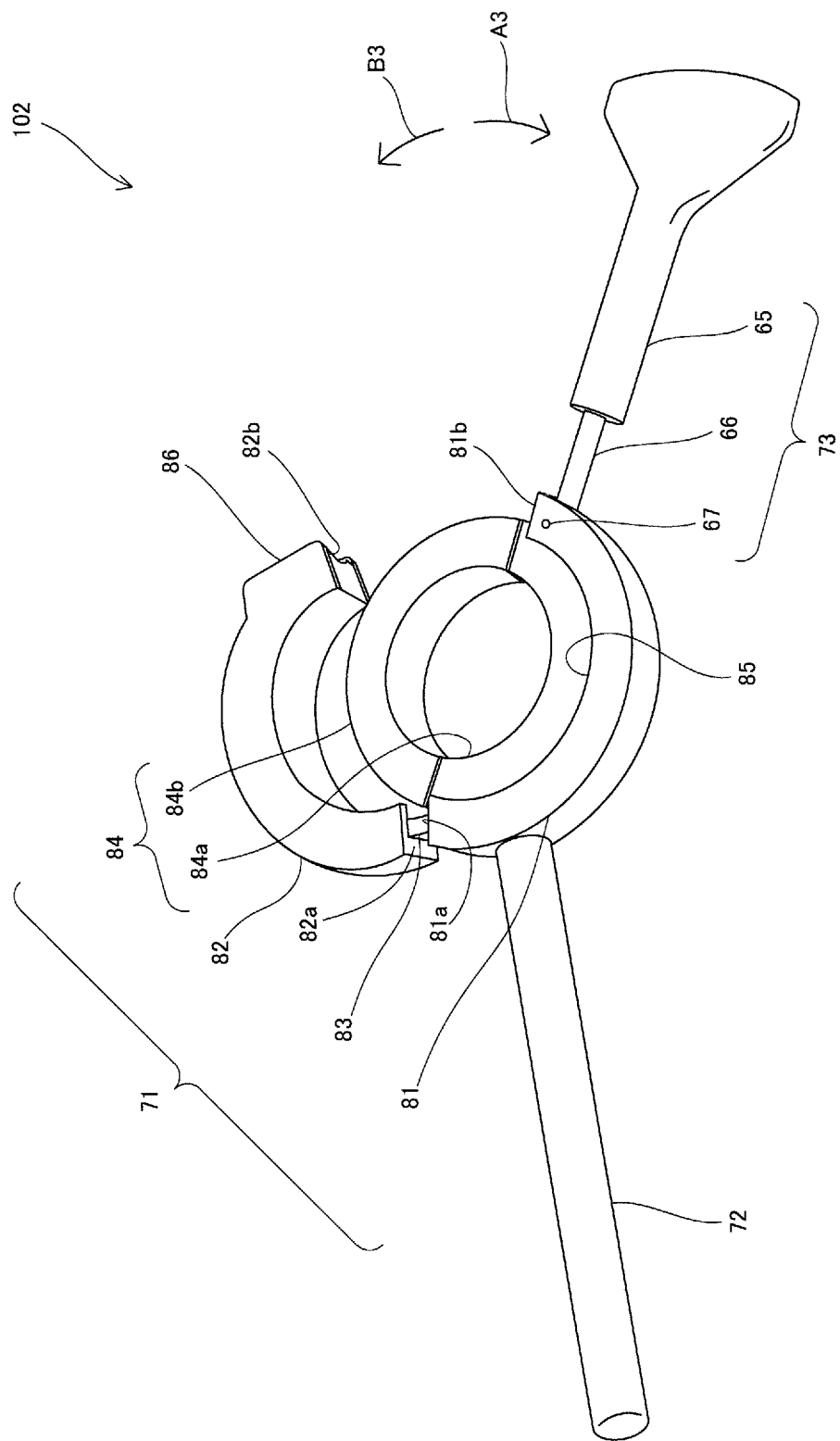
FIG. 15 is a perspective view showing a gripping portion of the gripping mechanism in FIG. 14 in an open state.

FIG. 14 is a perspective view showing the gripping mechanism 102 according to an embodiment of the present invention. FIG. 15 is a perspective view showing a gripping portion 71 of the gripping mechanism 102 in FIG. 14 in an open state.

As shown in FIGS. 14 and 15, the gripping mechanism 102 includes a gripping portion 71, a fixing member 73, and a supporting portion 106.

(a) Gripping Portion and Fixing Member

The gripping portion 71 is a ring-shaped member, for example, and includes a first constituent member 81, a second constituent member 82, a hinge portion 83, and an adjustment member 84. Note that the gripping portion 71 is not limited to being ring-shaped, and may have a multangular shape or the like.

The first constituent member 81 and the second constituent member 82 are substantially C-shaped, and an opening portion 85 is formed in the gripping portion 71 as a result of the first constituent member 81 and the second constituent member 82 being coupled to each other.

A first end 81a of the first constituent member 81 and a first end 82a of the second constituent member 82 are coupled to each other via the hinge portion 83. Also, a second end 81b of the first constituent member 81 and a second end 82b of the second constituent member 82 can be coupled to, and decoupled from, each other.

A state where the second end 81b of the first constituent member 81 and the second end 82b of the second constituent member 82 are coupled to each other is hereinafter referred to as "a closed state". Note that, in a state where the second end 81b of the first constituent member 81 and the second end 82b of the second constituent member 82 are coupled to each other, a small gap may be present between the second end 81b and the second end 82b.

Also, a state where the second end 81b of the first constituent member 81 and the second end 82b of the second constituent member 82 are decoupled from each other, i.e. a state where the second end 81b of the first constituent member 81 and the second end 82b of the second constituent member 82 are separate from each other is hereinafter referred to as "an open state".

The fixing member 73 is a screw, for example, and includes a body portion 65, a shaft portion 66, and a pivot portion 67. The body portion 65 and the shaft portion 66 are pivotable about the pivot portion 67 provided in the first constituent member 81, in the directions indicated by an arrow A3 and an arrow B3 shown in FIG. 15.

Also, a second constituent member 82 is provided with a fitting portion 86 into which the shaft portion 66 can be fitted. When the gripping portion 71 is in a closed state, it is possible to keep the gripping portion 71 in a closed state by pivoting the body portion 65 and the shaft portion 66 in the direction indicated by the arrow B3, and fitting the shaft portion 66 into the fitting portion 86. Also, it is possible to release the gripping portion 71 from a closed state by pivoting the body portion 65 and the shaft portion 66 in the direction indicated by the arrow A3 and detaching the shaft portion 66 from the fitting portion 86.

The fixing member 73 is not limited to a screw, provided that it is a member that can keep the gripping portion 71 in a closed state or release the gripping portion 71 from a closed state.

Note that the gripping portion 71 does not necessarily include a plurality of constituent members, specifically the first constituent member 81 and the second constituent member 82, provided that an opening portion is formed in the gripping portion 71 and the gripping portion 71 can grip the outer tube 12 in the opening portion. Also, if the gripping portion 71 does not include a plurality of constituent members, the gripping mechanism 102 does not need to include the fixing member 73.

The adjustment member 84 is ring-shaped, for example, and is attachable to, and detachable from, the opening portion 85. The adjustment member 84 includes a first curved member 84a that is substantially C-shaped, and a second curved member 84b that is substantially C-shaped.

The first curved member 84a and the second curved member 84b can be coupled to, and decoupled from, each other. As a result of the first curved member 84a and the second curved member 84b being coupled to each other, a through hole into which the outer tube 12 can be inserted is formed. The first curved member 84a and the second curved member 84b are not limited to being C-shaped, and may have a multangular shape or the like.

To place the medical instrument 101 so as to be gripped by the gripping mechanism 102, specifically, an operator such as an assistant first detaches the shaft portion 66 from the fitting portion 86 to release the gripping portion 71 from a closed state, and bring the gripping portion 71 into an open state.

Next, the operator detaches the first curved member 84a or the second curved member 84b from the opening portion 85. In this example, the operator detaches the second curved member 84b from the opening portion 85.

Next, the operator bring the outer circumferential surface of the outer tube 12 into contact with the inner circumferential surface of the first curved member 84a that is attached to the opening portion 85.

Next, the operator attaches the second curved member 84b, which has been detached from the opening portion 85, to the opening portion 85 such that the outer tube 12 is sandwiched between the first curved member 84a and the second curved member 84b, to couple the first curved member 84a and the second curved member 84b to each other.

Next, the operator couples the second end 81b of the first constituent member 81 and the second end 81b of the second constituent member 82 to each other, to bring the gripping portion 71 into a closed state. Next, the operator fits the shaft portion 66 of the fixing member 73 into the fitting portion 86 of the second constituent member 82 to keep the gripping portion 71 in a closed state. Thus, the medical instrument 101 is kept in a state of being gripped by the gripping mechanism 102.

(b) Adjustment of Diameter of Opening Portion

A plurality of types of adjustment members 84 with different inner diameters are prepared, for example. As described above, outer tubes 12 with different outer diameters may be used depending on the part inside the body cavity where the medical instrument 101 is to be inserted. Therefore, the operator selects and uses an appropriate adjustment member 84 from among a plurality of types of adjustment members 84 depending on the outer diameter of the outer tube 12 that is to be used.

Note that if the diameter of the opening portion 85 can be changed, there is no need to prepare a plurality of types of adjustment members 84 with different inner diameters. For example, by detaching the adjustment member 84 from the opening portion 85 and placing the outer tube 12 such that the outer circumferential surface thereof directly abuts against the inner circumferential surface of the gripping portion 71, it is possible to grip an outer tube 12 with a larger outer diameter compared to when the adjustment member 84 is attached to the opening portion 85.

Also, for example, the gripping portion 71 may include, instead of the adjustment member 84, a claw portion that is configured to be able to protrude toward a central point of the opening portion 85, and the gripping portion 71 may be configured to be able to change the diameter of the opening portion 85 by changing the amount of protrusion of the claw portion.

(c) Supporting Portion

The supporting portion 106 includes a connecting portion 72 and the coupling 105. The connecting portion 72 is connected to the gripping portion 71. The connecting portion 72 is rod-shaped, for example, and extends from the outer circumferential surface of the gripping portion 71. Note that the connecting portion 72 is not limited to being rod-shaped, and may be a protrusion that protrudes from the outer circumferential surface of the gripping portion 71, for example.

Although the connecting portion 72 shown in FIGS. 14 and 15 is provided so as to be in parallel with the open face defined by the opening portion 85, the connecting portion 72 is not necessarily parallel with the open face. Also, as shown in FIG. 14, in a state where the shaft portion 66 of the fixing member 73 is fitted into the fitting portion 86, the connecting portion 72 opposes the body portion 65 of the fixing member 73 with the opening portion 85 interposed therebetween, for example.

Also, as shown in FIG. 14, the connecting portion 72 is connected to the coupling 105. The coupling 105 includes a plurality of arm portions 91. Also, the coupling 105 includes one or more joint portions 92 that make it possible to adjust the position and orientation of the medical instrument 101. The plurality of arm portions 91 are coupled to one another via the joint portions 92.

More specifically, for example, each arm portion 91 is configured to be pivotable about a joint portion 92. Also, each joint portion 92 can fix the position and orientation of arm portions 91 relative to itself. Thus, it is possible to adjust the position and orientation of each of the plurality of arm portions 91 coupled to one another via the joint portions 92. Therefore, it is possible to freely adjust the position and orientation of the medical instrument 101.

When surgery is to be performed, the operator places the medical instrument 101 so as to be gripped by the gripping portion 71, and thereafter connects the connecting portion 72 to the coupling 105. Next, the operator adjusts the position and orientation of each of the plurality of arm portions 91 of the coupling 105, thereby adjusting the position and orientation of the medical instrument 101 such that the medical instrument 101 gripped by the gripping portion 71 gets close to the surgical site.

Note that a member that has a ring shape or the like and that includes the gripping portion 71 may be directly connected to the coupling 105. If this is the case, the supporting portion 106 is constituted by the coupling 105, and the supporting portion 106 is directly connected to the gripping portion 71.

Incidentally, when surgery is to be performed using a medical instrument such as the endoscope treatment device disclosed in Patent Document 1 that includes an outer tube into which inner tubes can be inserted, the medical instrument is attached to the body by, for example, inserting the outer tube into a trocar that is held on the body surface, by inserting the medical instrument into a mouthpiece as described in Patent Document 1, or by an assistant or the like holding the medical instrument by his/her hand. Therefore, an operator needs to get used to attaching or holding the medical instrument, and there is the possibility of shake, displacement, or the like.

On the other hand, the gripping mechanism 102 according to the embodiment of the present invention includes: an inner tube 11 into which a surgical instrument 1 can be inserted and that is flexible; and an outer tube 12 into which one or more inner tubes 11 can be inserted and that is to be inserted into a body cavity. The gripping mechanism 102 includes a gripping portion 71 that grips the outer tube 12, and a supporting portion 106 that fixes and supports the gripping portion 71. The supporting portion 106 includes at least one joint portion 92 that makes the medical instrument 101 adjustable regarding the position and orientation thereof.

With such a configuration, it is unnecessary to manually grip the medical instrument 101, and it is possible to more reliably fix the position and orientation of the medical instrument 101. Also, for example, by adjusting the position and orientation of each of the plurality of arm portions 91 in the supporting portion 106, it is possible to freely adjust the position and orientation of the medical instrument 101 gripped by the gripping portion 71. According to the present invention, it is possible to perform more desirable treatment using the medical instrument 101 that includes the outer tube 12 into which the inner tubes 11 can be inserted.

In particular, if motors are provided to drive the above-described inner tubes 11, the weight of the medical instrument 101 increases, and it becomes difficult to hold the medical instrument 101 by using a conventional cannula or by hand. Therefore, it is effective that the gripping mechanism 102 according to the embodiment of the present invention is employed.

Also, the above-described gripping mechanism 102 is used to grip an outer tube 12 into which a plurality of inner tubes 11 are inserted so as to be replaceable, and is particularly effective in laparoscopic surgery in which there is no support like a mouthpiece and the outer tube 12 is likely to move during treatment.

Although the present invention has been described and illustrated in detail, it is clearly understood that the same is by way of illustration and example only and is not to be taken by way of limitation, the scope of the present invention being interpreted by the terms of the appended claims.

The invention claimed is:

1. A surgical system comprising:
   a plurality of surgical instruments each of which includes a flexible shaft provided with a surgical tool on a leading end-side portion thereof;
   a supporting platform that supports the plurality of surgical instruments;
   a medical instrument that includes a plurality of flexible inner tubes into which the flexible shafts of the plurality of surgical instruments can be inserted, and an outer tube into which the plurality of flexible inner tubes can be inserted and that is to be inserted into a patient; and
   a gripping mechanism that includes a gripping portion that grips the outer tube, and a supporting portion that includes at least one joint portion and that fixes and supports the gripping portion, the at least one joint portion making the medical instrument adjustable regarding a position and orientation thereof, wherein
   the plurality of surgical instruments comprise a plurality of surgical instrument drive mechanisms each of which is housed in a surgical instrument drive mechanism housing and includes at least one built-in motor provided in the respective housing of the surgical instrument drive mechanism, wherein the at least one built-in motor of each surgical instrument drive mechanism is coupled to the surgical tool of a corresponding one of the plurality of surgical instruments via a wire and drives the surgical tool, and
   the surgical system further comprises first external motors provided outside the housings of the plurality of the surgical instrument drive mechanisms, wherein the first external motors are coupled to the plurality of surgical instrument drive mechanisms and rotate the plurality of surgical instrument drive mechanisms about axes of the respective flexible shafts.

2. The surgical system according to claim 1, further comprising:
second external motors that are provided outside the housings of the surgical instrument drive mechanisms, wherein the second external motors are coupled to the plurality of surgical instrument drive mechanisms and slide the plurality of surgical instrument drive mechanisms in axial directions of the respective flexible shafts.

3. The surgical system according to claim 1,
wherein the gripping portion includes
an opening portion into which the outer tube can be inserted, and
an adjustment mechanism that can change a diameter of the opening portion.

4. The surgical system according to claim 3,
wherein the adjustment mechanism is an adjustment member that is attachable to, and detachable from, the opening portion, and the diameter of the opening portion can be changed by attaching or detaching the adjustment member to or from the opening portion.

5. The surgical system according to claim 3,
wherein the adjustment mechanism is a claw portion that is formed so as to be able to protrude toward a central point of the opening portion, and an amount of protrusion of the claw portion is changeable.

6. The surgical system according to claim 3,
wherein the gripping portion includes a plurality of constituent members that can be coupled to each other,
the opening portion is formed by coupling the plurality of constituent members to each other, and
the gripping mechanism further includes a fixing member for fixing the plurality of constituent members in a state of being coupled to each other.

7. The surgical system according to claim 6,
wherein the supporting portion includes a coupling and a connecting portion, the coupling including the joint portion and a plurality of arm portions that are coupled to each other via the joint portion, and the connecting portion connecting the coupling and the gripping portion to each other, and
the fixing member opposes the connecting portion with the opening portion interposed therebetween.

8. The surgical system according to claim 1,
wherein the gripping portion is ring-shaped.

9. The surgical system according to claim 1,
wherein the supporting portion includes a coupling, the coupling including the joint portion and a plurality of arm portions that are coupled to each other via the joint portion.

10. The surgical system according to claim 9,
wherein the supporting portion further includes a connecting portion that connects the coupling and the gripping portion to each other.

11. The surgical system according to claim 10,
wherein the connecting portion is rod-shaped, and extends from an outer circumferential surface of the gripping portion.

12. The surgical system according to claim 1,
wherein the medical instrument is an instrument that is to be used in laparoscopic surgery.

13. The surgical system according to claim 1,
wherein each of the plurality of surgical instruments includes the flexible shaft, a multi-joint portion provided on the leading end-side portion of the flexible shaft, a wrist portion provided on a leading end-side portion of the multi-joint portion, and the surgical tool provided on a leading end-side portion of the wrist portion, and
wherein the at least one built-in motor comprises a plurality of built-in motors coupled to the surgical tool, the multi-joint portion, and the wrist portion and configured to independently drive the surgical tool, the multi-joint portion, and the wrist portion.

* * * * *